US011559074B2

(12) United States Patent
Passe

(10) Patent No.: US 11,559,074 B2
(45) Date of Patent: Jan. 24, 2023

(54) LIPID-RICH MICROALGAL FLOUR AND METHOD FOR PREPARING SAME

(71) Applicant: Corbion Biotech, Inc., South San Francisco, CA (US)

(72) Inventor: Damien Passe, Douai (FR)

(73) Assignee: Corbion Biotech, Inc., South San Francisco, CA (US)

( * ) Notice: Subject to any disclaimer, the term of this patent is extended or adjusted under 35 U.S.C. 154(b) by 927 days.

(21) Appl. No.: 14/905,342

(22) PCT Filed: Jul. 17, 2014

(86) PCT No.: PCT/FR2014/051841
§ 371 (c)(1),
(2) Date: Jan. 15, 2016

(87) PCT Pub. No.: WO2015/007999
PCT Pub. Date: Jan. 22, 2015

(65) Prior Publication Data
US 2016/0143337 A1    May 26, 2016

(30) Foreign Application Priority Data
Jul. 19, 2013  (FR) ........................................ 1357110

(51) Int. Cl.
*A23L 17/60* (2016.01)
*A23L 29/00* (2016.01)
*A61K 36/05* (2006.01)

(52) U.S. Cl.
CPC ............. *A23L 17/60* (2016.08); *A23L 29/065* (2016.08); *A23V 2002/00* (2013.01); *A61K 36/05* (2013.01)

(58) Field of Classification Search
CPC ....................................................... A23L 1/28
See application file for complete search history.

(56) References Cited

U.S. PATENT DOCUMENTS

| | | | |
|---|---|---|---|
| 3,962,466 A * | 6/1976 | Nakabayashi | A23J 1/18 426/60 |
| 4,564,526 A | 1/1986 | Takashima | |
| 4,917,915 A | 4/1990 | Cain et al. | |
| 4,978,553 A | 12/1990 | Silver | |
| 5,346,716 A | 9/1994 | Bakal et al. | |
| 5,487,916 A | 1/1996 | Christensen | |
| 5,512,311 A | 4/1996 | Capitani et al. | |
| 5,547,699 A | 8/1996 | Iizuka et al. | |
| 5,693,357 A | 12/1997 | Wong et al. | |
| 5,792,631 A | 8/1998 | Running | |
| 6,255,505 B1 | 7/2001 | Bijl et al. | |
| 6,372,460 B1 | 4/2002 | Gladue et al. | |
| 6,607,900 B2 | 8/2003 | Bailey et al. | |
| 8,709,750 B2 | 4/2014 | Gordon et al. | |
| 2002/0068110 A1 | 6/2002 | Liu et al. | |
| 2007/0099280 A1 | 5/2007 | Barclay | |
| 2009/0286295 A1 | 11/2009 | Medoff et al. | |
| 2010/0297292 A1 | 11/2010 | Brooks et al. | |
| 2010/0297295 A1 | 11/2010 | Brooks et al. | |
| 2010/0297296 A1 | 11/2010 | Brooks et al. | |
| 2010/0297323 A1 | 11/2010 | Brooks et al. | |
| 2010/0297325 A1 | 11/2010 | Brooks et al. | |
| 2010/0297331 A1 | 11/2010 | Brooks et al. | |
| 2010/0303957 A1 | 12/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2011/0256282 A1 | 10/2011 | Piechocki et al. | |
| 2011/0305740 A1 | 12/2011 | Boursier et al. | |
| 2011/0311599 A1 | 12/2011 | Boursier et al. | |
| 2012/0128851 A1 | 5/2012 | Brooks et al. | |
| 2013/0122180 A1 | 5/2013 | Brooks et al. | |
| 2014/0106051 A1 | 4/2014 | Lefevre et al. | |
| 2015/0272136 A1 | 10/2015 | Guillemant et al. | |
| 2016/0015071 A1 | 1/2016 | Delebarre et al. | |
| 2016/0021893 A1 | 1/2016 | Delebarre et al. | |
| 2016/0021895 A1 | 1/2016 | Leroux et al. | |
| 2016/0029684 A1 | 2/2016 | Passe | |

(Continued)

FOREIGN PATENT DOCUMENTS

| | | |
|---|---|---|
| CN | 1596694 | 3/2005 |
| CN | 102643714 A | 8/2012 |

(Continued)

OTHER PUBLICATIONS

Ryckebosch, Influence of Draying and Storage on Lipid and Carotenoid Stability of Micoralga Phaedoctyylum tricnutum, Journal of Ag and Food Chem, 2011, 59 11063-11069 accessed at https://pubs.acs.org/doi/ipdf/10.1021/jf2025456 (Year: 2011).*
Anon, BETE Spray Dry Manual, BETE Fog Nozzle, 2005, p. 1-25 (Year: 2005).*
International Search Report PCT/FR2014/051841 dated Feb. 4, 2015.
Anonymous: "Solazyme Roquette Nutritionals Golden Chlorella Omega to be key ingredient in Natural Vitality Release of new 30oz Bottle for Energy28 Golden", Mar. 10, 2011, XP055110155.
Elaine Watson: "Solazyme Breaking News on Food & Beverage Development—North America Special Edition: Protein-Rich Foods . . . The Next Generation Could algae be the new big thing in the protein market? Part one: Solazyme Roquette Nutritionals", Jan. 23, 2013, XP055110159.

(Continued)

*Primary Examiner* — Donald R Spamer
*Assistant Examiner* — Philip A Dubois
(74) *Attorney, Agent, or Firm* — Leydig, Voit & Mayer

(57) ABSTRACT

A microalgal flour having a particle size of between 30 and 150 μm and compressibility, measured by way of POWDER TESTER HOSOKAWA, of between 45 and 55%, has a flow value, determined according to a test A, of between 55 and 60% by weight for residue at 2,000 μm, dispersibility and wettability, expressed according to a test B, by the height of the product decanted in a beaker, of a value of between 0 and 2 mm; and a degree of humidification of a value of more than 70%, and preferably of more than 80%, of the total powder.

3 Claims, No Drawings

(56) References Cited

U.S. PATENT DOCUMENTS

| | | | |
|---|---|---|---|
| 2016/0324167 | A1 | 11/2016 | Brooks et al. |
| 2016/0374379 | A1 | 12/2016 | Passe et al. |
| 2018/0139994 | A1 | 5/2018 | Brooks et al. |
| 2018/0213831 | A1 | 8/2018 | Delebarre |
| 2018/0228188 | A1 | 8/2018 | Delebarre et al. |

FOREIGN PATENT DOCUMENTS

| | | |
|---|---|---|
| DE | 102006056454 | 5/2008 |
| EP | 0 622 027 A2 | 11/1994 |
| EP | 1 853 124 B1 | 9/2008 |
| EP | 2 183 977 A1 | 5/2010 |
| FR | 2 924 126 A1 | 5/2009 |
| JP | 360075244 | 10/1983 |
| JP | 409252707 A | 9/1997 |
| JP | 2012-505656 | 3/2012 |
| JP | 2012-519011 | 8/2012 |
| JP | 2012-519013 | 8/2012 |
| JP | 2012-523843 | 10/2012 |
| WO | WO 98/09700 | 3/1998 |
| WO | WO 2001/44440 | 6/2001 |
| WO | WO 2006/122299 | 11/2006 |
| WO | WO 2010/045368 | 4/2010 |
| WO | WO 2010/100368 | 9/2010 |
| WO | WO 2010/100369 | 9/2010 |
| WO | WO 2010/120923 | 10/2010 |
| WO | WO 2011/108919 | 9/2011 |
| WO | WO 2011/130578 | 10/2011 |
| WO | 2011/150411 | 12/2011 |
| WO | WO 2012/095121 A1 | 7/2012 |
| WO | WO 2014/062882 | 4/2014 |
| WO | WO 2014/064231 | 5/2014 |
| WO | WO 2014/117163 A1 | 7/2014 |
| WO | WO 2014/140242 | 9/2014 |
| WO | WO 2014/140244 | 9/2014 |
| WO | WO 2014/140245 | 9/2014 |
| WO | WO 2014/140247 | 9/2014 |
| WO | WO 2015/007999 A2 | 1/2015 |
| WO | WO 2015/079169 | 6/2015 |

OTHER PUBLICATIONS

U.S. Appl. No. 14/056,100, Request for Restriction Requirement, dated Sep. 21, 2016.
U.S. Appl. No. 14/056,100, Non-Final Office Action, dated Apr. 4, 2017.
Restriction Requirement, dated Apr. 10, 2017, in U.S. Appl. No. 14/438,239.
Non-Final Rejection, dated Jan. 12, 2018, in U.S. Appl. No. 14/438,239.
Restriction Requirement, dated Sep. 5, 2017, in U.S. Appl. No. 14/776,751.
Non-Final Rejection, dated Apr. 2, 2018, in U.S. Appl. No. 14/776,751.
Non-Final Rejection, dated Apr. 28, 2017, in U.S. Appl. No. 14/776,930.
Final Rejection, dated Aug. 21, 2017, in U.S. Appl. No. 14/776,930.
Non-Final Rejection, dated Dec. 21, 2017, in U.S. Appl. No. 14/776,930.
Final Rejection, dated Jun. 20, 2018, in U.S. Appl. No. 14/776,930.
Non-Final Rejection, dated Sep. 15, 2017, in U.S. Appl. No. 14/776,962.
Non-Final Rejection, dated Dec. 9, 2016, in U.S. Appl. No. 14/776,962.
Final Rejection, dated Nov. 17, 2017, in U.S. Appl. No. 14/776,962.
Final Rejection, dated May 1, 2017, in U.S. Appl. No. 14/776,962.
Restriction Requirement, dated May 30, 2017, in U.S. Appl. No. 14/776,949.
Non-Final Rejection, dated Jul. 10, 2017, in U.S. Appl. No. 14/776,949.
Final Rejection, dated Oct. 31, 2017, in U.S. Appl. No. 14/776,949.
Non-Final Rejection, dated Jun. 15, 2018, in U.S. Appl. No. 15/955,468.
Non-Final Rejection, dated Sep. 19, 2018, in U.S. Appl. No. 15/039,868.
Final Rejection, dated Oct. 10, 2018, in U.S. Appl. No. 14/438,239.
Final Rejection, dated Sep. 26, 2018, in U.S. Appl. No. 14/045,100.
International Search Report, dated Feb. 6, 2014, for International Application No. PCT/EP2013/072343, pp. 1-8.
Written Opinion in International Application No. PCT/EP2013/072343, dated Feb. 6, 2014, pp. 1-8.
International Search Report, dated May 27, 2014, for International Application No. PCT/EP2014/055057, pp. 1-8.
Written Opinion in International Application No. PCT/EP2014/055057, dated May 27, 2014, pp. 1-8.
International Search Report, dated May 30, 2014, for International Application No. PCT/EP2014/055063, pp. 1-8 and English Translation.
Written Opinion in International Application No. PCT/EP2014/055063, dated May 30, 2014, pp. 1-8 and English Translation.
International Search Report, dated Jun. 16, 2014, from International Application No. PCT/EP2014/055060, pp. 1-8 and English Translation.
Written Opinion in International Application No. PCT/EP2014/055060, dated Jun. 16, 2014, pp. 1-8 and English Translation.
International Search Report, dated Jun. 16, 2014, from International Application No. PCT/EP2014/055061, pp. 1-9 and English Translation.
Written Opinion in International Application No. PCT/EP2014/055061, dated Jun. 16, 2014, pp. 1-9 and English Translation.
Written Opinion, dated Feb. 4, 2015, from International Patent Application No. PCT/FR14/051841, filed Jul. 17, 2014 and English Translation.
International Search Report, dated Feb. 16, 2015, from corresponding PCT application, (International Patent Application No. PCT/FR14/53052, filed Nov. 27, 2014) and English Translation.
Written Opinion, dated Feb. 16, 2015, from corresponding PCT application, (International Patent Application No. PCT/FR14/53052, filed Nov. 27, 2014) and English Translation.
Australian Patent Application No. 2013331243, Patent Examination Report No. 1, dated May 30, 2016.
Australian Patent Application No. 2013331243, Patent Examination Report No. 2, dated Feb. 8, 2017.
Australian Patent Application No. 2013331243, Patent Examination Report No. 3, dated May 4, 2017.
Chinese Patent Application No. 201380054255.X, Notification of First Office Action, dated Nov. 28, 2016.
Chinese Patent Application No. 201380054255.X, Notification of Second Office Action, dated Aug. 8, 2017.
Chinese Patent Application No. 201380054255.X, Notification of Third Office Action, dated Feb. 1, 2018.
Supplemental European Search Report, dated Apr. 25, 2016, for European Patent Application No. 13 84 7337.
Extended European Search Report, dated May 3, 2016, including the Supplemental European Examination Report, dated Apr. 25, 2016, for European Patent Application No. 13 84 7337.
Examination Report, dated Nov. 30, 2017, for European Patent Application No. 13 84 7337.
International Search Report, dated Feb. 21, 2014, for International Patent Application No. PCT/US2013/65369.
Written Opinion of the International Searching Authority, dated Feb. 21, 2014, for International Patent Application No. PCT/US2013/65369.
International Preliminary Examination Report, dated Apr. 21, 2015, for International Patent Application No. PCT/US2013/65369.
Notice for Reasons for Rejection, dated Aug. 31, 2017, for Japanese Patent Application No. 2015-537812, with English Translation.
Notice for Reasons for Rejection, dated Mar. 30, 2018, for Japanese Patent Application No. 2015-537812, with English Translation.
Notice for Reasons for Rejection, dated Apr. 18, 2018, for Japanese Patent Application No. 2017-128829 (in Japanese).
First Examination Report, dated Feb. 7, 2018, for New Zealand Patent Application No. 707192.
Japanese Patent Application No. JP 2015-562181, 1st Notice of Reasons for Rejection, dated Oct. 4, 2017, No. Translation.

(56) References Cited

OTHER PUBLICATIONS

Japanese Patent Application No. JP 2015-562181, 2nd Notice of Reasons for Rejection, dated Jun. 14, 2018, with English Translation.
Chinese Patent Application No. 201480014074.9, Decision of Rejection, dated Jan. 15, 2018, with English translation.
European Patent Application No. EP 14 711 947.3, Office Action, dated Dec. 5, 2017. (in French).
Japanese Patent Application No. JP 2015-562178, Notice of Reasons for Rejection, dated Nov. 22, 2018, with English translation.
Further Examination Report, dated Aug. 8, 2018, for New Zealand Patent Application No. 707192.
Communication pursuant to Article 94(3) EPC, dated Aug. 14, 2018, for Europrean Patent Application No. 13 847 337.
Chinese Patent Application No. 201380054255.X, Rejection Decision, dated Aug. 28, 2018.
Batista, A.P., et al., "Microalgae bioactive components for innovative food products development," 37th WEFTA Meeting Book of Abstracts, INRB/IPIMAR, Abstract S3.14, p. 134, (2007).
Becker, E.W., "Micro-algae as a source of protein," Biotechnology Advances,vol. 25; No. 2, pp. 207-201, (Jan. 26, 2007).
Belasco, Warren, "Algae Burgers for a Hungry World? The Rise and Fall of Chlorella Cuisine," Technology and Culture, 38(3):608-634, (1997).
Chacón-Lee, T.L. and G.E. González-Mariño, "Microalgae for "Healthy" Foods—Possibilities and Challenges", Comprehensive Reviews in Food Science and Food Safety, vol. 9; (Oct. 31, 2010), pp. 655-675.
Database WPI, AN 1978-43554A, Week 1978, XP002724795, Thomson Scientific, London, Great Britain, Aug. 5, 1977, p. 1.
Database WPI, AN 2005-480030, Week 200549, XP002694315, Thomson Scientific, London, Great Britain, Mar. 23, 2015, p. 1.
Database WPI, AN 2013-e 16999, Week 2013, XP002725042, Thomson Scientific, London, Great Britain, Apr. 9, 2012, p. 1.
Fradique et al., "Microalgae biomass incorporation in pasta products," 5th Pigments in Food congress—for quality and health, ISBN 978-952-10-4846-3, p. 182, (Aug. 2008). Abstract.
Gouveia et al., "Chlorella vulgaris and Haematococcus pluvialis biomass as colouring and antioxidant in food emulsions," Eur Food Res Technol, 222:362-367, (2006).
Gouveia, L. et al., "Microalgae in Novel Food Products," Food Chemistry Research Developments, Chapter 2, Nova Science Publishers, Inc., ISBN 978-1-60456-262-0, 37 pages, (May 2008).
Krüger, "Kurze Charakteristik einiger niedrerer Organismen im Saftfluss der Laubbäume," Hedwigia, 33: 241-266, (1894). Machine Translation.
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of Chlorella Protothecoides," J. Biotech., 110:85-93, (2004).
Raymundo et al., "Fat mimetic capacity of Chlorella vulgaris biomass in oil-in-water food emulsions stabilized by pea protein," Food Research International, 38:961-965, (Feb. 25, 2005).
Samarasinghe, Nalin, et al., "Algal Cell Rupture Using High Pressure Homogenization as a Prelude to Oil Extraction." Renewable Energy, vol. 48, (Apr. 20, 2012) pp. 300-308, 2012.
Shi et al., "Production and rapid extraction of lutein and the other lipid-soluble pigments from Chlorella protothecoides grown under heterotrophic and mixotrophic conditions," Nahrung, 43:109-113, (1999).
Shi, et al., "Production of biomass and lutein by Chlorella protothecoides at various glucose concentrations in heterotrophic cultures", Process Biochemistry, 34:341-347, (1999).
Solazyme, Inc. "Algal Flour (*Chlorella*) GRAS Notice," Mar. 16, 2010, pp. 1-74, retrieved from the internet on May 23, 2014t: http://www.fda.gov/ucm/groups/fdagov-public/@fdagov-foods-gen/documents/document/ucm269513.pdf.

Spiden, Erin M. et al., "Quantitative Evaluation of the Ease of Rupture of Industrially Promising Microalgae by High Pressure Homogenization." Bioresource Technology, vol. 140, pp. 165-171, (Apr. 28, 2013).
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (Mar. 1, 1994).
Xu, H., et al., "High Quality Biodiesel Production from a Microalgal Chlorella Protothecoides by Heterotrophic Growth in Fermenters." Journal of Biotechnology, vol. 126, pp. 499-507, (2006).
Bisten A and H.Schuchmann, "Optical measuring methods for the investigation of high-pressure homogenization", Processes, (Nov. 15, 2016) ;4(4):41.
Memorandum Order, *Roquette Frères, S.A. v. Solazyme, Inc.*, C.A. No. 14-1442-SLR, District Court for the District of Delaware, Jan. 12, 2016.
Plaintiff and Counter-Defendant Roquette Frères, S.A.'s Reply Brief in Support of its Motion for Stay Pending Appeal, *Roquette Frères, S.A. v. Solazyme, Inc.*, C.A. No. 14-1442-SLR, District Court for the District of Delaware, Jan. 8, 2016.
Defendant and Counterclaimant Solazyme, Inc.'s Brief in Opposition to Plaintiff and Counter-Defendant Roquette Freres, S.A.'s Motion to Stay Pending Appeal, *Roquette Frères, S.A. v. Solazyme, Inc.*, C.A. No. 14-1442-SLR, District Court for the District of Delaware, Jan. 6, 2016.
Declaration of Jonathan Wolfson in Support of Defendant and Counterclaimant Solazyme, Inc.'s Opposition to Plaintiff and Counterclaimant Roquette Freres, S.A.'s Motion to Stay Pending Appeal, *Roquette Frères, S.A. v. Solazyme, Inc.*, C.A. No. 14-1442-SLR, District Court for the District of Delaware, Jan. 6, 2016, Redacted Public Version.
Declaration of Jeffrey M. Goehring in Support of Plaintiff and Counter-Defendant Roquette Frères, S.A.'s Brief Motion for Stay Pending Appeal, *Roquette Frères, S.A. v. Solazyme, Inc.*, C.A. No. 14-1442-SLR, District Court for the District of Delaware, Dec. 28, 2015, Redacted Version • Exhibit 1, BASF and Solazyme Launch the First Commercial Microalgae-Derived Betaine Surfactant, Solazyme, Inc., Jul. 28, 2015 • Exhibit 2, Solazyme Bunge Renewable Oils Completes Key Redundant Power and Steam Supplies, Solazyme Bunge Renewable Oils, Jun. 30, 2015 • Exhibit 3, Solazyme Receives FDA GRAS No Questions Letter for High Oleic Algae Oil, Solazyme, Inc., Feb. 24, 2015 • Exhibit 4, Solazyme's (SZYM) CEO Jonathan Wolfson on Q1 2015 Results—Earnings Call Transcript, Solazyme, Inc., May 6, 2015 • Exhibit 5, Solazyme's (SZYM) CEO Jonathan Wolfson on Q2 2015 Results—Earnings Call Transcript, Solazyme, Inc., Jul. 30, 2015 • Exhibit 6, Solazyme's (SZYM) CEO Jonathan Wolfson on Q4 2014 Results—Earnings Call Transcript, Solazyme, Feb. 26, 2015 • Exhibit 7, Redacted in its Entirety.
Motion to Stay Pending Appeal and Order Granting Motion to Stay Pending Appeal, *Roquette Frères, S.A. v. Solazyme, Inc.*, C.A. No. 14-1442-SLR, District Court for the District of Delaware, Dec. 28, 2015.
Memorandum of Law in Support of Motion by Roquette Frères, S.A. for a Stay Pending Appeal, *Roquette Frères, S.A. v. Solazyme, Inc.*, C.A. No. 14-1442-SLR, District Court for the District of Delaware, Dec. 28, 2015.
Email dated Nov. 3, 2015, from Gerald Suh of Solazyme, Inc., to Jeffrey M. Goehring of Young & Thompson International Patent & Trademark Law (counsel for Roquette Frères, S.A.).
Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures:• Exhibits 1, 9-12, and 14-15 to the Declaration of Jeffrey M. Goehring in Support of

(56) References Cited

OTHER PUBLICATIONS

Roquette Frères, S.A.'s Brief in Support of its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 141, Jun. 22, 2015, Redacted Version• Exhibits 2-8 to the Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112-1, Jun. 22, 2015• Exhibit 13 to the Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112-2, Jun. 22, 2015• Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112, Jun. 22, 2015• Roquette Frères, S.A.'s Opening Brief in Support of its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 140, Jun. 22, 2015, Redacted Version.

Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.

Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).

Opinion dated Dec. 21, 2015 in *Roquette Frères, S.A., v. Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.

Youzhi Jiagong, (Jun. 8, 2007), "Oil Processing Technology (2nd edition)", Chemical Industry Press, Title page, Publication Page, Table of Contents, pp. 206-213, (in Chinese).

"Linoleic acid and α-linolenic acid are real essential fatty acids", (Mar. 1998), Title page, Publication Page, Table of Contents, Chapter 2: Essential Fatty Acids (pp. 12-13) and Chapter 15: Selection of the most suitable fatty acids (pp. 89-91), with English translation.

Bowman, Barbara A. and Robert M. Russell (eds.), "Present Knowledge in Nutrition" (1st Edition), (Oct. 2004), Title page, Publication Page, Table of Contents, p. 231 (in Chinese).

"Auxenochlorella", article from Wikipedia, Retrieved from the Internet on Mar. 23, 2016, "https://en.wikipedia.org/w/index.php?title=Auxenochlorella&oldid=711518993".

Clore, G.M. and E.M. Chance, A computer analysis of cyanide stimulated oxygen uptake in *Chlorella protothecoides*. (Jul. 1977) FEBS Lett. 79 (2):353-356.

"Algen—Nudein ais Altmark Spezialitat (Algae noodles: a speciality from Altmark region)" in German language, and other *Chlorella* Food products, (Oct. 9, 2007), 3 pages.

Imai, Ichiro, et al. "Advanced research on Shellfish poisonings: Current Status and overview", Table of Contents, Chapters 1 and Chapter 4, 11 pages.

"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].

Lee, Yuan-Kun, "Commercial Production of microalgae in the Asia-Pacific rim", Journal of Applied Phycology, 9:403-411, (Oct. 29, 1997).

Kay, Robert A., "Microalgae as Food and Supplement", Critical Reviews in Food Science and Nutrition, 30(6):555-573 (Feb. 1991).

Usuki, Riichiro and Luniko Kamata,"Experimental Trials on the Role of Lipids in Good Taste and Good Body of Foods", Research reports of Shokei Gakuin College 53, May 2006, p. 85-90 (in Japanese with English Abstract).

"Chlorella Photosynthesis—Dictionary", last modified Mar. 23, 2015, Retrevied from the Internet: <URL: (http://photosyn.jp/pwiki/index.php?%E3%82%AF%E3%83%AD%E3%83%AC%E3%83%A9) with English Machine Translation.

Hirashima, Ryuta, "Framework of evaluation on inventive step requirement and significance of 'technical problem'", Patent 2010, 63(5): 34-49 (in Japanese; no translation).

Ullmann, Jorg, "The Difference between *Chlorella* vulgaris and *Chlorella* pyrenoidosa", (2006) (http://www.algomed.de/index.php?op=algenfarm_geschichte).

"History of the algae farm: Chlorella Algae—Roquette Klötze GmbH", [Retrieved from the Internet Nov. 25, 2016: <URL: (http://www.algomed.de/index.php?op=algenfarm_geschichte)].

Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.

Oral Summary, dated Nov. 7, 2016, for Invalidation Hearing for Japanese Patent No. 5731982 (in Japanese).

Oral Summary by the Patentee, dated Nov. 29, 2016, for Invalidation Hearing for Japanese Patent No. 5731982 (in Japanese).

USDA National Nutrient Database (https://ndb.nal.usda.gov/ndb/).

Environmental Stresses in Non Mammalian Organisms, p. 29. with English translation.

Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013).

Solazyme Market and Products, (2005).

Letter from Susan Cho to Susan Carlson, dated Jul. 25, 2011 and "RFI's Chlorella vulgaris GRAS Self affirmation (dated Jul. 16, 2010)."

[Retrieved from the Internet Oct. 13, 2016: <URL: http://hfnet.nih.go.jp/contents/detail105.htm] (in Chinese).

"Roquette Freres, S.A. and Solazyme, Inc. Agree to Dissolve Microalgae Join Venture", (Jun. 24, 2013) Press Release, Lestrem, France.

Standard Tables of Food Composition in Japan 2015 (Seventh Revised Edition), Table of Fatty Acid Composition, Edited by The Council for Science and Technology, the Ministry of Education, Culture, Sports, Science and Technology, (available from http://www.mext.go.jp/a_menu/syokuhinseibun/1365295.htm) [Retrieved from the Internet Oct. 12, 2016: <URL: (http://www.algomed.de/index.php?op=algenfarm_geschichte)] http://www.geocities.jp/jr2bvb/syokuhin/sibousan/oil_s.htm].

"'Taste' of Lipids?" [Retrieved from the Internet Oct. 12, 2016: <URL: (https://sites.google.com/site/coffeetambe/coffeescience/physiology/taste/fat] with English Machine Translation.

Japanese Laid-Open Publication No. 2000-175680 (translator's note: an English language member of the same patent family: EP 1142985 (A1)).

Japanese Laid-Open Publication No. 2002-223787 (translator's note: no English language counterpart could be located).

http://mcc.nies.go.jp/strainList.do?strainId=2555&condition=Auxenochlorella+protothecoides.

http://mcc.nies.go.jp/strainList.do?strainId=2568&condition=Auxenochlorella+protothecoides.

*Roquette Freres S.A. v. Solazyme Inc.*, Delaware District Court, Case No. 1:14-cv-01442 District Judge Sue L. Robinson, presiding, Solazyme, Inc.'s Answer to Plaintiff Roquette Freres, S.A.'s Complaint, Petition to Confirm Arbitration Award and Counterclaims, filed Feb. 26, 2015, 29 pages.

(56) References Cited

OTHER PUBLICATIONS

Joint Venture and Operating agreement of Solazyme Roquette Nutritionals, LLC., dated Nov. 7, 2015.
*Solazyme, Inc.* vs. *Roquette Freres, S.A.*, Arbitration Award, dated Feb. 19, 2015.
Request for Invalidation, dated Jan. 7, 2015, for Chinese Patent Application No. 200980149978.1, 21 pages (in Chinese).
Supplemental Statement for Request for Invalidation, dated Dec. 2, 2015, for Chinese Patent Application No. 200980149978.1, 35 pages (in Chinese), including the list of submitted Counter Evidences on p. 1-2.
Notification of Acceptance of Request for Invalidation, dated Jan. 28, 2016, for Chinese Patent Application No. 200980149978.1, 4 pages (in Chinese).
Documents filed by the Petitioner—Part II, dated Apr. 29, 2015, for Chinese Patent Application No. 200980149978.1, 21 pages (in Chinese), including : • Jia, Xuan, et al., "Removal of Total nitrogen form wastewater discharge from a chemical pertilizer plant by Chlorella protothecoides USTB-01", Chinese Journal of Environmental Engineering, (Apr. 2010), 4(4):737-740 (in Chinese).
Documents filed by the Petitioner—Part III, dated May 5, 2015, for Chinese Patent Application No. 200980149978.1, 21 pages (in Chinese), including : , including : • Singelton Paul and Diana Sainsbury, "Dictionary of Microbiological and Molecular Biology, (3rd Ed. 2006)", pp. 155 (and Chinese translation thereof) • Singelton Paul and Diana Sainsbury, "Dictionary of Microbiological and Molecular Biology, (2nd Ed. 1987)", pp. 178-179 (and Chinese translation thereof).
Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonwealth of Australia Mar. 3, 2016, (21 pages).
Declaration of Michael Armin Borowitzka in the matter of Australian Patent Application No. 2009303354 in the name of Solazyme, Inc. and Opposition by *Roquette Frères, S.A.* v. *Solazyme, Inc.*, Commonwealth of Australia Jun. 2, 2016, (32 pages).
• Exhibit MB-1, Federal Court of Australia, Practice Note CM7, Expert Witnesses in Proceedings on the Federal Court of Australia, commenes Jun. 4, 2013 • Exhibit MB-2, Michael Armin Borowitzka Curriculum Vitae • Exhibit MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. • Exhibit MB-4, Krauss, Robert W., "Mass Culture of Algae for Food and Other Organic Compounds," American Journal of Botany, vol. 49, No. 4 (Apr. 1962), pp. 425-435. • Exhibit MB-5, Lee, Yuan-Kun, "Commercial Production of microalgae in the Asia-Pacific rim", Journal of Applied Phycology, 9:403-411, (Oct. 29, 1997) • Exhibit MB-6, Soong, Pinnan, "Productions and Development of *Chlorella* and *Spirulina* in Taiwan", Algae Biomass: Production and Use, Gedaliah Shelef and Carl J. Soeder (eds.), North-Holland Biomedical Press, (Dec. 1980), pp. 97-113 and title and copyright page. • Exhibit MB-7, Kawaguchi, Kotaro, "Microalgae Production Systems in Asia", Algae Biomass: Production and Use, Gedaliah Shelef and Carl J. Soeder (eds.), North-Holland Biomedical Press, (Dec. 1980), pp. 25-33 and title and copyright page. • Exhibit MB-8, Kay, Robert A., "Microalgae as Food and Supplement", Critical Reviews in Food Science and Nutrition, 30(6):555-573 (Feb. 1991). • Exhibit MB-9, Raymundo et al., "Fat mimetic capacity of Chlorella vulgaris biomass in oil-in-water food emulsions stabilized by pea protein," Food Research International, 38:961-965, (Feb. 25, 2005). • Exhibit MB-10, Samejima, H. and J Myers, "On the Heterotrophic Growth of Chlorella *pyrenoidosa*", J. Gen Microbiol, (1958), 18:107-117.
• Exhibit MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retrieved from the internet on Jun. 7, 2013 from http://pcp.oxfordjournals.org/ by Reprints Desk ]. • Exhibit MB-12, Becker, E.W., "Micro-algae as a source of protein," Biotechnology Advances, 25:207-201, (Mar.-Apr. 2007). • Exhibit MB-13, Iwamoto, Hiroaki, "Industrial Production of Microalgal Cell-mass and Secondary Products— Major Industrial Species Chlorella", Chapter 11, Handbook of Microalgal Culture: Biotechnology and Applied Phycology, Amos Richmond (eds), (Dec. 1, 2003), pp. 255-263. • Exhibit MB-14, Petkov et al., "Which are fatty acids of the green alga Chlorella?," Biochemical Systematics and Ecology, 35:281-285, (2007). • Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21, 1995), 31:774-777. • Exhibit MB-16, Xu et al., "High Quality Biodiesel Production From a Microalga Chlorella Protothecoides by Heterotrophic Growth in Fermenters," Journal of Biotechnology, 126(4):499-507, (May 2006). • Exhibit MB-17, Matsuka et al., "Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966). • Exhibit MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740.
• Exhibit MB-19, Australian Application No. 2009303354B2 from International Patent Application No. PCT/US2009/060692, naming Solazyme, Inc., International Patent Publication No. 2010/045368, dated Apr. 22, 2010. • Exhibit MB-20, Pabst, W., "Nutritional evaluation of nonsewage microalgae by the rat balance method," Arch. HyrobioL Beih, (Dec. 1978), pp. 65-70 • Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000).
• Exhibit MB-22, Kamiya, "Effects of Blue Light and Ammonia on Nitrogen Metabolism in a Colorless Mutant of Chlorella", Plant Cell Phyiol., 30(4):513-521 (1989) • Exhibit MB-23, Biello et al., "Biofuel of the Future: Oil from Algae," Scientific American, 2 pages (Jan. 9, 2008).
Evidence in Support, In the matter of Australian Patent Application No. 2009303354 in the name of Solazyme, Inc. and Opposition by *Roquette Frères, S.A.* v. *Solazyme, Inc.*, Commonwealth of Australia, Jun. 3, 2016, (1 page).
Declaration of Young J. Suh In the matter of Australian Patent Application No. 2009303354 in the name of Solazyme, Inc. and Opposition by *Roquette Frères, S.A.* v. *Solazyme, Inc.*, Commonwealth of Australia, Aug. 31, 2016, (94 pages)• Exhibit YS1, Arbitration Award, *Solazyme Inc.* vs. *Roquette Frères*, Case 1:14-cv-O1442-SLR, Document 153, Filed Dec. 21, 2015 • Exhibit YS2, French Patent Publication No. FR 2 924 126, filed Nov. 28, 2007.
• Exhibit YS3, Memorandum Opinion, Document 153, *Roquette Frères, S.A.* vs. *Solazyme Inc.*, Case 1:14-cv-O1442-SLR, filed Dec. 21, 2015.
Declaration of Craig Patch in the matter of Australian Patent Application No. 2009303354 in the name of Solazyme, Inc. and Opposition by *Roquette Frères, S.A.* v. *Solazyme, Inc.*, Commonwealth of Australia, Sep. 5, 2016, (22 pages) Exhibit CP-1, Federal Court of Australia, Practice Note CM7, Expert Witnesses in Proceedings on the Federal Court of Australia, commences Jun. 4, 2013. • Exhibit CP-2, Craig Patch Curriculum Vitae.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 28, 2016, (42 pages). • Exhibit CP3, Record of Views Formed in Response to Inquires, updated Mar. 2015 (20 pages) • Exhibit CP4, Huss, V.A.R., et al., "Biochemical Taxonomy and Molecular Phylogeny of the Genus *Chlorella sensu lato* (Chlorophyta)1", J. Phycol. 35, 587-598 (Jan. 15, 1999).
Evidence in Answer, In the matter of Australian Patent Application No. 2009303354 in the name of Solazyme, Inc. and Opposition by *Roquette Frères, S.A.* v. *Solazyme, Inc.*, Commonwealth of Australia, Sep. 29, 2016, (1 page).
Declaration of Michael Armin Borowitzka In the matter of Australian Patent Application No. 2009303354 in the name of Solazyme, Inc. and Opposition by *Roquette Frères, S.A.* v. *Solazyme, Inc.*, Commonwealth of Australia, Dec. 21, 2016, (14 pages).

(56) References Cited

OTHER PUBLICATIONS

Evidence in Reply, In the matter of Australian Patent Application No. 2009303354 in the name of Solazyme, Inc. and Opposition by *Roquette Frères, S.A.* v. *Solazyme, Inc.*, Commonwealth of Australia Dec. 23, 2016, (1 page).

"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.

Freshwater Algae Culture Collection at the Institute of Hydrobiology (FACHB-collection), certification letter by the Chinse Academy of Science, "Chlorella vulgaris", (No Date).

Zhou, Lian-ning et al. "Effects of Environmental Factors on Nitrogen and Phosphorus Removal by *Chlorella vulgaris* in Wastewater", Current Biotechnology, (Jan. 25, 2015), vol. 5, No. 1, Title page, Publication Page, Table of Contents (I Chinese and English), pp. 60-65, with English abstract.

Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.

First Statement, Substantive Brief, filed with IP High Court Case No. H29 (gyo-ke) 10149 on Nov. 17, 2017 in Invalidation Appeal No. 2016-800012 against Japanese Patent No. 5731982, with English translation.

Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.

Opponent's Outline of Submissions, In the Matter of Australian Patent Application No. 2009303354 in the name of Corbion Biotech, Inc., dated Jan. 24, 2018, 48 pages.

Response to REG 5.23 Request, In the Matter of Australian Patent Application No. 2009303354 in the name of Corbion Biotech, Inc., filed Feb. 5, 2018, 18 pages. • Letter from David Sieveking, dated Jan. 24, 2018 • Statutory Declaration of Dr. Daniel Peter Sieveking, dated Jan. 24, 2018. Exhibit DS-1, Kyle, David, "Production and Use of Lipids from Microalgae", Microalgal Lipids, Lipid Technology, (May-Jun. 1992), pp. 59-64. Exhibit DK-2, Chen et al., "High cell density culture of microalgae in heterotrophic growth," Trends in Biotechnology, 14:421-426, (1996).

Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only.

Request for Withdrawal of Opposition, by Roquette Freres, to Grant of Australian Patent Application No. 2009303354, in the Name of Corbion Biotech, Inc., dated Mar. 13, 2018.

Opposition Proceedings, dated Mar. 14, 2018, Acknowledgement of the the Request for Withdrawal of Opposition, by Roquette Freres, to Grant of Australian Patent Application No. 2009303354.

Third Party Observations from Roquette Freres, dated Aug. 31, 2017, for Chinese patent for invention No. 200980149978.1 (in Japanese with English Translation).

Third Party Observations from Roquette Freres, dated Aug. 31, 2017, for Chinese patent for invention No. 201080026237.7 (in Japanese with English Translation).

International Bureau, International Preliminary Report on Patentability in International Application No. PCT/FR2014/051841, dated Jan. 19, 2016.

"Enter the World of Microalgae," Roquette (Jun. 2014).

\* cited by examiner

LIPID-RICH MICROALGAL FLOUR AND METHOD FOR PREPARING SAME

The present invention relates to a lipid-rich microalgal flour, the microalgae being of the *Chlorella* genus, preferably *Chlorella protothecoides*.

More particularly the present invention relates to a lipid-rich microalgal flour having, for a given particle size distribution and compression values, flow, wettability and water-dispersibility properties which are quite noteworthy.

PRESENTATION OF THE PRIOR ART

There are several species of algae that can be used in food, most being "macroalgae" such as kelp, sea lettuce (*Ulva lactuca*) and red food algae of the type Porphyra (cultured in Japan) or "dulse" (red alga, *Palmaria palmata*).

However, alongside these macroalgae are also several sources of algae represented by the "microalgae", i.e. microscopic unicellular algae which may be photosynthetic or non-photosynthetic, of marine or non-marine origin cultured for their applications in biofuel, food, cosmetics or nutritional health.

For example, spirulina (*Arthrospira platensis*) is cultured in open lagoons (under phototrophic conditions) for use as a food supplement or incorporated in small amounts into confectionery products or drinks (generally less than 0.5% w/w).

Other lipid-rich microalgae, including certain species of *Chlorella*, are also very popular in Asian countries as food supplements (mention may be made of microalgae of the *Crypthecodinium* or *Schizochytrium genera*).

The oil fraction of the *Chlorella* biomass, which is composed essentially of monounsaturated oils, thus provides nutritional and health advantages compared with the saturated, hydrogenated and polyunsaturated oils often found in conventional food products.

Chlorellae are thus utilized in food for human or animal consumption, either in the form of whole biomass or in the form of flour, obtained by drying the biomass of chlorellae, the cell walls of which have been broken by in particular mechanical means.

The microalgal flour also provides other benefits, such as micronutrients, dietary fibers (soluble and insoluble carbohydrates), phospholipids, glycoproteins, phytosterols, tocopherols, tocotrienols and selenium.

In order to prepare the biomass which will be incorporated into the composition of foods, the biomass is concentrated, or harvested, from the culture medium (culturing by photoautotrophy in photobioreactors, or heterotrophically in darkness and in the presence of a source of carbon which can be assimilated by the chlorellae).

In the technical field to which the invention relates, the heterotrophic growth of chlorellae is preferred (what is known as the fermenting route).

At the time of the harvesting of the microalgal biomass from the fermentation medium, the biomass comprises intact cells which are mostly in suspension in an aqueous culture medium.

In order to concentrate the biomass, a solid-liquid separation step is then carried out by frontal or tangential filtration, or by centrifugation by any means known, moreover, to those skilled in the art.

After concentration, the microalgal biomass can be treated directly in order to produce vacuum-packed cakes, algal flakes, algal homogenates, intact-algae powder, milled-algae flour or algal oil.

The microalgal biomass is also dried in order to facilitate the subsequent treatment or for use of the biomass in its various applications, in particular food applications.

Various textures and flavors can be conferred on food products, depending on whether the algal biomass is dried, and if it is, depending on the drying method used.

For example, patent U.S. Pat. No. 6,607,900 describes drying the microalgal biomass using a drum dryer without any prior centrifugation, in order to prepare microalgal flakes.

Microalgal powder may be prepared from biomass of microalgae which have been concentrated, using a pneumatic dryer or by spray drying, as described in patent U.S. Pat. No. 6,372,460.

In a spray dryer, a liquid suspension is then sprayed in the form of a dispersion of fine droplets in a stream of heated air. The entrained material is rapidly dried and forms a dry powder.

In other instances, a combination of spray drying followed by the use of a fluidized bed dryer is used to achieve improved conditions for obtaining a dried microalgal biomass (see, for example, patent U.S. Pat. No. 6,255,505).

In the technical field to which the invention relates, it is more particularly sought to prepare a flour of algae produced by the fermenting route.

This microalgal flour within the context of the invention is prepared from the concentrated microalgal biomass which has been mechanically lyzed and homogenized, the homogenate then being spray dried or flash dried.

The production of algal flour requires the cells to be lyzed in order to release their oil.

For example, a pressure disruptor can be used to pump a suspension containing the cells through a restricted orifice so as to lyze the cells.

A high pressure (up to 1500 bar) is applied, followed by an instantaneous expansion through a nozzle.

The cells can be broken by three different mechanisms: running into the valve, high shear of the liquid in the orifice, and a sudden drop in pressure at the outlet, causing the cell to explode.

The method releases the intracellular molecules.

A Niro homogenizer (GEA Niro Soavi or any other high-pressure homogenizer) may be used to treat cells having a size predominantly between 0.2 and 5 microns.

This treatment of the algal biomass under high pressure (approximately 1000 bar) generally lyzes more than 90% of the cells and reduces the size to less than 5 microns.

Alternatively, a ball mill is instead used.

In a ball mill, the cells are agitated in suspension with small spherical particles. The breaking of the cells is caused by the shear forces, the milling between the balls, and the collisions with balls.

These balls break the cells so as to release the cell content therefrom. The description of an appropriate ball mill is, for example, given in patent U.S. Pat. No. 5,330,913.

A suspension of particles of smaller size than the cells of origin is obtained in the form of an "oil-in-water" emulsion.

This emulsion is then spray dried and the water is eliminated, leaving a dry powder containing the cell debris, intracellular liquid and oil.

However, the production of a dry powder which is sticky, clumps together and flows with difficulty, since it contains oil in a content of 10%, 25% or even 50% by weight of the dry powder, is highly undesirable.

High lipids contents (more than 60%) are even considered to be more difficult or even impossible to dry effectively.

Problems of wettability and water-dispersibility of the dried biomass flours, which then have poorer wettability properties, are also highly undesirable.

In order to solve the inherent difficulties in drying these lipid-rich emulsions, a person skilled in the art generally follows two main routes:
- choosing drying devices adapted to powders rich in fats, with a particular implementation;
- using various flow agents (for example, silica-based products) or spray drying supports;
- the formulation (by encapsulation) without these two routes being mutually exclusive.

Spray Drying Devices

There are several devices in the prior art for spray drying lipid-rich compounds. It is possible to readily find in the literature illustrations of the technology and equipment proposed: for example, in the *Spray Drying Handbook* by K. Masters, in particular in the 5$^{th}$ edition thereof, published in 1991 and republished in 1994 by Longman Scientific & Technical (available at the British Library or at the Library of Congress under ISBN 0-470-21743-X), or in the BETE® Spray Dry Manual, 2005 (accessed at the website www-.bete.com).

It thus appears, upon reading these documents, that none of the proposed solutions is entirely satisfactory, for example:
- for drying milk products enriched in fats (20%-30%), co-current spray drying towers equipped with spraying nozzles are conventionally used, in a two-stage device (the second stage being assigned to conditioning and cooling the powder obtained in the first stage).

However, deposits form readily and increase the risk of fire breaking out by mechanisms of auto-oxidation, which entails the addition of multiple fire extinguishing systems;
- for drying processed cheese, the cheese is milled and mixed with water to form a smooth cream before spray drying. The spray drying is then carried out in a conical-bottomed spray dryer.

However, again due to the high fat content, deposits form.

The proposed solution is to use spray dryers equipped with fluidized beds or moving belts fitted in the base of the spray dryer chamber.

However, problems of pneumatic conveying of the dried powder thus obtained still remain;
- for drying non-milk ice creams, in which vegetable fats replace butter, and sodium caseinates replace the non-fat milk solids, the difficulty with spray drying is due to the high sugar content (conventionally greater than 30%).

It is then necessary to carry out the spray drying in the presence of a portion of the sugar, and to supplement the formulation by adding superfine sugar to the dry mixture.

Moreover, to overcome the problems of high sugar content, it is necessary to be able to control the production of dust, manage the pneumatic conveying of the powder, limit the agglomeration thereof and avoid deposits inside the spray drying chamber.

However, only solutions for drying in a spray drying chamber equipped with a fluidized bed have been proposed;
- for drying products having from 35% to 80% fats, the problem which must be avoided is that of breaking the protective membranes of the lipid globules (in particular proteins) which leads to the release of said fats during drying.

The recommended solution is an increase in the melting point of the lipids, the formation or the integration into the spray dryer of a cooling bed system at the base of the spray drying chamber.

Alternatively, the air introduced at the base of said spray drying chamber may be cooled by secondary air in order to prevent the powder melting in the chamber, and in order to solidify the surface of the particles before any mechanical manipulation.

Again alternatively, if cyclones are provided for collecting the powder, it is necessary to introduce cold air before any collection, in order to prevent melting inside the cyclones.

Finally, it is preferred to implement a complex configuration combining a spray drying tower comprising nozzles, with an integrated fluidized bed or a moving belt;
for drying algae.

Especially described in the literature, as described hereinabove, is the drying of whole microalgae, which microalgae are of the genera *Chlorella* and *Spirulina*.

The powder form thereof is then intended for making tablets for preparing food supplements in dietetics.

The spray drying is then carried out on biomasses of low solids content (10%-15%) in a turbine spray dryer equipped with an open cycle co-current spray drying chamber.

On account of this low solids content, only a powder of fine particle size is then produced.

Drying Additives

In the field of coffee/tea whiteners, these are compositions which combine sodium caseinate, corn syrup, vegetable fats with emulsifiers, potassium phosphate and sodium aluminum silicates.

The spray drying is carried out in two-stage co-current spray dryers equipped with vibrating external fluidized beds.

Particles with a fine particle size are produced.

In order to obtain agglomerated particles, dryers are chosen in which the fluidized bed and the moving belt are integrated.

In the field of vegetable oils, the drying of olive oil moreover requires the use of spray drying supports such as maltodextrins.

Subject of the Invention

There is therefore still an unmet need for novel stabilized forms of lipid-rich microalgal biomass flour, in order to make it possible to easily incorporate them, on a large scale, into food products which must remain delicious and nutritious.

The applicant company has therefore found that this need could be met by proposing a lipid-rich microalgal flour having, for a given particle size distribution and given compression values, flow, wettability and water-dispersibility properties which are quite noteworthy.

In other words, the lipid-rich microalgal flour of the invention has a particle size and compression properties which are equivalent to a standard lipid-rich microalgal flour, but associated with noteworthy flow, wettability and water-dispersibility properties.

The microalgal flour according to the invention, the size of the flour particles being between 30 and 150 µm in diameter and said flour having a compressibility, measured on a HOSOKAWA powder tester, of between 45% and 55%, is therefore characterized in that it has:
a flow value, determined according to a test A, of between 55% and 60% by weight for the oversize at 2000 µm,
a dispersibility and a wettability, expressed, according to a test B, by:

the height of the product decanted in a beaker, having a value of between 0 and 2 mm;

a degree of wetting having a value of more than 70%, preferably more than 80% of the total powder.

Preferably the microalgae are of the *Chlorella* genus, preferably *Chlorella protothecoides*.

Moreover, the microalgal flour, and in particular the microalgal biomass, comprises at least 10%, 20%, 30%, 40%, 50% or 60% by dry weight of lipids.

The microalgal flour according to the invention is moreover able to be prepared by a process using flat-bottom spray dryer technology coupled to an air broom for sweeping the spray drying chamber with low-pressure air.

As will be demonstrated hereinafter, this drying is executed particularly meticulously to obtain the flour of the invention, with regards to:

the ratio of the flow rate of the main drying air from the flat-bottom spray dryer to the flow rate of the air from the air broom, the temperature of the air from the air broom.

Thus, the present invention relates to a process for preparing the microalgal flour according to the present invention, characterized in that it comprises:

1) preparing an emulsion of lipid-rich microalgal flour in water with a solids content of between 15% and 50% by dry weight,
2) introducing this emulsion into a high-pressure homogenizer,
3) spraying this emulsion in a flat-bottom spray dryer equipped with an air broom for sweeping the spray drying chamber with low-pressure air in its lower portion, while making adjustments to ensure that:
   a) the temperature of the main drying air is between 160 and 240° C.,
   b) the temperature of the air in the air broom portion is at most 70° C., preferably at most 65° C., more preferably between 50 and 60° C.,
   c) the ratio of the flow rate of the air from the air broom to the flow rate of the main drying air has a value greater than ⅓, preferably between ⅓ and ½,
   d) the temperature of the cooling air is between 25 and 35° C., such that the flour leaving the spray dryer has a temperature of between 60° C. and 90° C.,
4) collecting the microalgal flour thus obtained.

Preferably, the microalgae are of the *Chlorella* genus, preferably *Chlorella protothecoides*. Moreover, the microalgae, and in particular the microalgal biomass, comprises at least 10%, 20%, 30%, 40%, 50% or 60% by dry weight of lipids.

The present invention also relates to the microalgal flour obtained by the process according to the present invention.

The present invention also relates to the use of the flour according to the present invention, or obtained by the process according to the present invention, in the food sectors. In particular, it relates to a method for preparing a food composition comprising the addition of such a microalgal flour to ingredients of the food composition.

DETAILED DESCRIPTION OF THE INVENTION

The present invention thus relates to the microalgal biomass suitable for human consumption which is rich in nutrients, in particular in lipids.

The invention more particularly relates to a microalgal flour which can be incorporated into food products in which the oil content of the microalgal flour can enable total or partial replacement of the oils and/or fats present in conventional food products.

For the purposes of the invention, the term "microalgal flour" means the dried product of breaking the cell walls of the microalgal biomass, in particular by mechanical means.

For the purposes of the invention, the microalgae under consideration are species which produce appropriate triglyceride oils and/or total lipids.

The microalgal biomass comprises at least 10% by dry weight of oils or lipids, preferably at least 25% to 35% or more by dry weight of oils or lipids.

More preferably still, the biomass contains at least 40%, at least 50%, at least 75% by dry weight of oils or lipids.

The preferred microalgae of the invention may grow in heterotrophic conditions (on sugars as source of carbon and in the absence of light).

The applicant company recommends choosing lipid-rich microalgae of the *Chlorella* genus.

The microalgae used may be chosen, non-exhaustively, from *Chlorella protothecoides, Chlorella kessleri, Chlorella minutissima, Chlorella* sp., *Chlorella sorokiniama, Chlorella luteoviridis, Chlorella vulgaris, Chlorella reisigffi, Chlorella effipsoidea, Chlorella saccarophila, Parachlorefia kessleri, Parachlorefia beijerinkii, Prototheca stagnora* and *Prototheca moriformis*. Preferably, the microalgae used according to the invention belong to the *Chlorella protothecoides* species.

The microalgae are cultured in liquid medium in order to produce the biomass as such.

According to the invention, the microalgae are cultured in a medium containing a carbon source and a nitrogen source in the absence of light (heterotrophic conditions).

The solid and liquid growth media are generally available in the literature, and the recommendations for preparing the particular media which are suitable for a large variety of microorganism strains can be found, for example, online at www.utex.org/, a website maintained by the University of Texas at Austin for its algal culture collection (UTEX).

The production of biomass is carried out in fermenters (or bioreactors).

The specific examples of bioreactors, the culture conditions, and the heterotrophic growth and methods of propagation can be combined in any appropriate manner in order to improve the efficiency of the microalgal growth and the lipids.

In the technical field to which the invention relates, it is sought to prepare an algal flour.

This microalgal flour within the context of the invention is prepared from the concentrated microalgal biomass which has been mechanically lyzed and homogenized, the homogenate then being dried.

The microalgal flour according to the invention, having a particle size between 30 and 150 μm and having a compressibility, measured on a HOSOKAWA powder tester, of between 45 and 55%, is characterized in that it has:

a flow value, determined according to a test A, of between 55% and 60% by weight for the oversize at 2000 μm, a dispersibility and a wettability, expressed, according to a test B, by:

the height of the product decanted in a beaker, having a value of between 0 and 2 mm;

a degree of wetting having a value of more than 70%, preferably more than 80% of the total powder.

In the technical field to which the invention relates, the microalgal flour has particle size and compression parameters which are commonly found in *Chlorella* microalgal flours dried by the conventional route (single-effect spray drying):

The microalgal flour according to the invention has a particle size of between 30 and 150 μm.

This measurement is carried out on a Coulter® LS laser particle size analyzer, equipped with its small volume dispersion module or SVM (125 ml), according to the constructor's specifications (in the "*Small Volume Module Operating instructions*").

The microalgal flour according to the invention has a compressibility, measured on a HOSOKAWA powder tester, of between 45% and 55%.

The compression or compressibility value C is obtained by calculating the ratio of the aerated bulk density value (=A) to the packed density value (=B), which are themselves determined using an apparatus sold by the company HOSOKAWA under the trade name Powder Tester, type PTE, by applying the method recommended in the operating instructions for measuring aerated bulk density and packed density, according to the following equation:

$$C = \frac{100(B-A)}{B}$$

By way of comparison, the compression value for a microalgal flour dried by single-effect spray drying is of the order of 47%.

However, surprisingly and unexpectedly, the microalgal flour in accordance with the invention is characterized by its noteworthy flow, wettability and dispersibility properties.

The microalgal flour according to the invention has flow properties, measured according to a test A, which are better than those measured for a microalgal flour dried by the conventional route.

The test A consists in measuring the degree of cohesion of the microalgal flour.

This cohesion test is inspired by the cohesion test described in the operating instructions of the Powder Characteristics Tester, type PTE, sold by the company HOSOKAWA.

The test A first of all consists in sieving the microalgal flour according to the invention on a sieve with a mesh opening of 800 μm.

The fraction of the flour having a size of less than 800 μm is then recovered and placed in a closed container, and undergoes mixing by epicycloidal motion using a Turbula laboratory mixer, type T2C.

By virtue of this mixing, according to its own characteristics, the microalgal flour in accordance with the invention will express its propensity to agglomerate or to repel.

The flour mixed in this way is then deposited on a 2000 μm sieve for another sieving operation.

Once the sieving has ended, the oversize on this sieve is quantified and the result gives an illustration of the "cohesive" or "tacky" nature of the microalgal flour.

Thus, a free-flowing powder, which is therefore not very cohesive, will virtually not be stopped by this sieve with wide openings.

The protocol is as follows:
sieving the required amount of product on an 800 μm sieve in order to recover 50 g of product having a size less than 800 μm, placing these 50 g of flour having a size of less than 800 μm in a glass jar with a volume of 1 liter (Ref. BVBL Verrerie Villeurbannaise-Villeurbanne France) and closing the lid, placing this jar in the mixer (Turbula, model T2C), adjusted to the speed of 42 rpm (Willy A. Bachofen Sarl-Sausheim-France) and mixing for 5 minutes, preparing the sieve (of the brand Saulas—Diameter 200 mm; Paisy Cosdon—France) which will be placed on a siever (Fritsch, model Pulverisette type 00.502); details of the assembly starting from the bottom to the top: siever, sieve bottom, 800 μm sieve, 2000 μm sieve, siever lid, depositing the powder resulting from the mixing on the top of the column (2000 μm sieve), closing with the siever lid and sieving for 5 minutes on the (Fritsch) siever, with an amplitude 5 in the permanent position, weighing the oversize on this sieve.

The microalgal flour therefore has between 55% and 60% by weight for the oversize at 2000 μm.

By way of comparison, the flow value for a conventional microalgal flour is of the order of 71%.

The microalgal flour according to the invention has quite noteworthy dispersibility and wettability properties.

This dispersibility and this wettability are expressed according to a test B, by:

the height of the product decanted in a beaker, having a value of between 0 and 2 mm;

a degree of wetting having a value of more than 70%, preferably more than 80% of the total powder.

This surprising and unexpected character is based on the fact that the compressibility and flow measurements demonstrate that the microalgal flour in accordance with the invention remains quite cohesive, just like the conventional microalgal flours, since after mixing, which does not use much mechanical energy (sieving time of barely 5 mins), 55% to 60% of the particles smaller than 800 μm still cannot pass through a 2000 μm sieve, the openings of which are nonetheless 2 to 4 times larger.

It is readily deduced therefrom that such a flour, exhibiting such a behavior, should be poorly dispersible and hence difficult to use in a preparation where uniform distribution of the ingredients is recommended.

Likewise, the wettability thereof should be low.

Wettability is a technological property very often used to characterize a powder resuspended in water, for example in dairy industries.

It reflects the ability of a powder to become immersed after having been deposited at the surface of water (Haugaard Sorensen et al., "Méthodes d'analyse des produits laitiers déshydratés" ["Methods for analyzing dehydrated milk products"], Niro A/S (publisher), Copenhagen, Denmark, 1978), and thus reflects the capacity of the powder to absorb water at its surface (Cayot and Lorient, "Structures et technofonctions des protéines du lait" ["Structures and technofunctions of milk proteins"]. Paris: Airlait Recherches: Tec and Doc, Lavoisier, 1998).

The measurement of this index conventionally consists in measuring the time required for a certain amount of powder to penetrate into the water through its free surface at rest.

According to Haugaard Sorensen et al. (1978):
a powder is said to be "wettable" if its "Index of Wettability"; is less than 20 seconds;
the swelling ability of the powder should also be associated with the wettability. This is because, when a powder absorbs water, it gradually swells. The structure of the powder then disappears when the various constituents are solubilized or dispersed.

This swelling ability is expressed as a % of wetted product.

Among the factors which influence wettability are the presence of large primary particles, the reintroduction of fines, the density of the powder, the porosity and the capillarity of the powder particles and also the presence of air, the presence of fats at the surface of the powder particles and the reconstitution conditions.

The test B, developed by the Applicant company, consists here in considering more particularly:
the behavior of the microalgal flour powder when brought into contact with water, by measuring, after a certain contact time, the height of the powder which decants when the powder is placed at the surface of the water;
its capacity for water uptake (expressed in %).

The protocol for this test is as follows:
500 ml of demineralized water at 20° C. are placed in a low-form beaker of 600 ml (Fischerbrand FB 33114 beaker),
25 g of the microalgal flour powder are uniformly placed at the surface of the water, without mixing,
the behavior of the powder over time is observed,
the height of the decanted product at the bottom of the beaker is measured.

A very cohesive powder of low wettability will remain at the surface of the liquid, while a powder of better wettability will decant more easily.

The microalgal flour according to the invention has a dispersibility and a wettability, expressed, according to the test B, by:
the height of the product decanted in a beaker, having a value of between 0 and 2 mm;
a degree of wetting having a value of more than 70%, preferably more than 80% of the total powder.

However, by way of comparison, the microalgal flour conventionally dried by single-effect spray drying stays at the surface of the water, and does not hydrate sufficiently to be able to decant to the bottom of the beaker.

The microalgal flour in accordance with the invention is able to be obtained by a particular way of conducting a process for spray drying, using a flat-bottom spray dryer (or FBSD) coupled to an air broom for sweeping the spray drying chamber with low-pressure air (or AB).

The flat-bottom spray dryer is conventionally used to dry fat-rich materials or hygroscopic products, or in a more practical sense, in places where there is a lack of space, etc. However, to the knowledge of the Applicant company, it has never been used coupled to an air broom for sweeping the spray drying chamber with low-pressure air for drying lyzed biomass of microalgae in general and *Chlorella* in particular.

With regard to the device coupling FBSD and AB, it is especially recommended for drying fruits, vegetable pulp and fruit juices, or even meat extracts.

In order to dry the lyzed microalgal biomass, following this principle of spray drying, it is possible to use for example an FBSD equipped with the AB sold by the companies CE Rogers, Marriott Walker, Henningsen Foods or Food Engineering Co. and Henszey Co.

Surprisingly and unexpectedly, the Applicant company thus observed that drying the microalgal flour by using, for example, this FBSD/AB process, made it possible not only to prepare a product with standard compressibility, particle size profile and flowability in a high yield, but especially to confer upon it unexpected flow, wettability and water-dispersibility properties, without it being necessary to use granulation binders or anti-caking agents.

Indeed, the processes described previously (such as single-effect spray drying which is conventionally used for drying biomasses or microalgal flours) do not make it possible to obtain all the desired characteristics.

The process for preparing the microalgal flour in accordance with the invention thus comprises the following steps:
1) preparing an emulsion of lipid-rich microalgal flour in water with a solids content of between 15% and 50% by dry weight,
2) introducing this emulsion into a high-pressure homogenizer,
3) spraying it in an FBSD equipped with an AB device in its lower portion, such that:
   a) the temperature of the main drying air is between 160 and 240° C.,
   b) the temperature of the air in the air broom portion is at most 70° C., preferably at most 65° C., more preferably between 50 and 60° C.,
   c) the ratio of the flow rate of the air from the AB to the flow rate of the main drying air has a value greater than ⅓, preferably between ⅓ and ½,
   d) the temperature of the cooling air is between 25 and 35° C., such that the flour leaving the spray dryer has a temperature of between 60° C. and 90° C.,
4) collecting the microalgal flour thus obtained.

The first step of the process of the invention consists in preparing an emulsion of lipid-rich microalgal flour in water with a solids content of between 15% and 50% by dry weight. In particular, the solids content may be between 25% and 45%, preferably between 35% and 45%. In addition, the lipid content of the microalgal flour or of the microalgal biomass is preferably a minimum of at least 10%, 20%, 30%, 40%, 50% or 60% by dry weight, for example between 20% and 80% or between 30% and 70%. Optionally, the degree of milling of the microalgal biomass may be at least from 25% to 75% of lyzed cells, for example 50%, 85% or 95% of cell lysis, and is preferably 85% or 95%.

As will be exemplified below, the biomass obtained at the end of fermentation typically has a lipid content of approximately 50%, from 10% to 50% fibers, 2% to 15% proteins, 30% sugars and 10% starch.

The biomass is then:
deactivated by flash heat treatment (HTST treatment),
washed by diluting with an aqueous solution and concentrating by centrifugation,
milled in a ball mill thus creating an "oil-in-water" emulsion.

The second step of the process of the invention consists in introducing this emulsion into a high pressure homogenizer.

The Applicant company recommends carrying out this homogenization of the emulsion in a two-stage device, for example a Gaulin homogenizer sold by the company APV, with a pressure of 160 bar at the first stage, and 40 bar at the second stage.

The third step of the process of the invention consists in spraying this solution in an FBSD equipped with an AB device in its lower portion, such that:
   a) the temperature of the main drying air is between 160 and 240° C.,
   b) the temperature of the air in the AB portion is at most 70° C., preferably at most 65° C., more preferably between 50 and 60° C.,
   c) the ratio of the flow rate of the air from the AB to the flow rate of the main drying air has a value greater than ⅓, preferably between ⅓ and ½, d) the temperature of the cooling air is between 25 and 35° C., such that the flour leaving the spray dryer has a temperature of between 60° C. and 90'C.

In this way, as will be exemplified below, for a flow rate of the main drying air fixed at 2200 kg/h, the flow rate of the air from the AB will be more than 750 kg/h, preferably between 800 and 900 kg/h.

As will also be exemplified below, these operating conditions make it possible to limit the formation of deposits on the walls of the spray drying chamber and thereby to optimize the drying yield at more than 90%, preferably at more than 95%, more preferably still at 99%.

Moreover, it is these parameters for controlling the AB, more than the act of spray drying in the FBSD, which make it possible to obtain products with such wettability and water-dispersibility properties.

The last step of the process in accordance with the invention consists, finally, in collecting the microalgal flour thus obtained.

This microalgal flour is of use in the food sector. Thus, the present invention relates to the use of the flour according to the present invention, or obtained by means of the process according to the present invention, in the food sectors. In particular, it relates to a method for preparing a food composition comprising the addition of such a microalgal flour to ingredients of the food composition or to the food composition. Such uses are, for example, described in patent applications WO 2010/045368, WO 2010/120923 or US 2010/0297296.

The invention will be understood more clearly from the examples which follow, which are intended to be illustrative and nonlimiting.

EXAMPLES

Example 1

Obtaining the *Chlorella protothecoides* Microalgal Biomass by Fermentation

The fermentation protocol is adapted from the one described entirely generally in patent application WO 2010/120923.

The production fermenter is inoculated with a pre-culture of *Chlorella protothecoides*. The volume after inoculation reaches 9000 l.

The carbon source used is a 55% w/w glucose syrup sterilized by application of a time/temperature scheme.

The fermentation is a fed-batch fermentation during which the glucose flow rate is adjusted so as to maintain a residual glucose concentration of from 3 to 10 g/l.

The production fermenter time is from 4 to 5 days.

At the end of fermentation, the cell concentration reaches 185 g/l.

During the glucose feed phase, the nitrogen content in the culture medium is limited so as to allow the accumulation of lipids in an amount of 50%.

The fermentation temperature is maintained at 28° C.

The fermentation pH before inoculation is adjusted to 6.8 and is then regulated on this same value during the fermentation.

The dissolved oxygen is maintained at a minimum of 30% by controlling the aeration, the counter pressure and the stirring of the fermenter.

The fermentation must is heat-treated over an HTST zone with a scheme of 1 min at 75° C. and cooled to 6° C.

The biomass is then washed with decarbonated drinking water with a dilution ratio of 6 to 1 (water/must) and concentrated to 250 g/l (25% DCW "Dry Cell Weight") by centrifugation using an Alfa Laval Feux 510.

The cells are deactivated by heat treatment through an HTST zone at 75° C. for 1 minute.

For the rest of the operations, the temperature is maintained under 8-10° C.

The concentration of interstitial soluble material is reduced by washing the biomass by diluting (3:1 ($V_{water}/V_{biomass}$)) and concentrating by centrifugation (disk-nozzle centrifuge).

After this step, the solids content of the biomass is approximately 25% at the separating outlet, then concentrated to 45% by evaporation.

The washed biomass is milled using a ball mill of bead mill type, with a degree of milling of 95%.

The coarse "oil-in-water" type emulsion produced in this way is homogenized under pressure in a two-stage Gaulin homogenizer (160 bar at the first stage/40 bar at the second stage) after adjusting the pH to 7 using potassium hydroxide.

The biomass obtained at the end of fermentation typically has a lipid content of approximately 50%, from 10% to 50% fibers, 2% to 15% proteins, 30% sugars and 10% starch, the percentages being expressed as dry weight of total biomass.

Example 2

Drying the Homogenized "Oil-in-Water" Emulsion of Microalgal Flour

The homogenized emulsion obtained in example 1 is dried:
in a single-effect spray dryer (liquid dried by a single pass through the flow of heat then recovered at the bottom of the tower at the cyclone or the sleeve filter), sold by GEA Niro, so as to obtain a control microalgal flour in accordance with what is commercially available.
Or
in a flat-bottom spray dryer equipped with an internal air broom for sweeping the spray drying chamber with low-pressure air, to obtain the microalgal flour in accordance with the invention.

The control single-effect spray drying operating conditions are as follows:
input temperature of 160° C.,
temperature of 60° C. in the drying section,
cooling temperature of the air: 21° C.
output temperature: 60° C.

With regard to the spray drying process in accordance with the invention, it consists in spraying the high-pressure-homogenized suspension in a flat-bottom spray dryer equipped with an air broom in the following manner:
Feed system: feed tank with helical mixer and heating jacket; mono pump; duplex filter
Spray dryer: Centrifuge, 160 mm in diameter,
Powder discharger: rotary device to avoid agglomeration at the bottom of the chamber,
Output air: air loaded with particles leaves the chamber at the bottom; the dry powder is separated from the air in a sleeve filter.

The parameters for executing spray drying in the flat-bottom spray dryer are as follows:

- Feed: emulsion with 20% solids at a temperature of 50-65° C.

turbine at 16 400 rpm
flow rate of the emulsion: 60 kg/h-160 kg/h
Main air:
  Flow rate: 2200 kg/h
  Temperature: 165-220° C.
Two configurations for executing the sweeping with air (air broom) are produced:
  1. standard execution,
  2. optimized execution to produce the microalgal flour in accordance with the invention.
The standard execution for sweeping with air (air broom) (according to the constructor's specifications) is as follows (for 1 test):
  air flow rate: 700 kg/h at a temperature of 70° C.
  Output temperature at the bottom of the chamber: 95° C.
  Cooling air: 600 kg/h at a temperature of 30° C.
  Air temperature before the sleeve filter: 81° C.
The production efficiency here is <90% and the formation of deposits on the walls of the spray drying chamber is observed.

The execution of sweeping with air (air broom) optimized by the Applicant company to give the microalgal flour in accordance with the invention is as follows (test carried out in triplicate):
  air flow rate: 850 kg/h at a temperature of 65° C.
  Cooling air: 800 kg/h at a temperature of 30° C.

The production efficiency here is 99% and the formation of deposits on the walls of the spray drying chamber is not observed.

Example 3

Characterizing the Microalgal Flour in Accordance with the Invention

In the table below, the values for the following parameters are presented:
  particle size,
  compressibility,
  flowability by cohesion test (2000 μm)
  wettability,
  water-dispersibility
for the "single-effect spray drying" control, for the non-optimized "air broom" control and for the three batches of microalgal flour in accordance with the invention.

|  | Particle size (D 4,3 - μm) | Aerated bulk density (g/ml) | Packed density (g/ml) | Compressibility (%) |
|---|---|---|---|---|
| Single-effect spray drying control | 40 | 0.27 | 0.51 | 47 |
| "Non-optimized" air broom control | 133 | 0.35 | 0.45 | 22 |
| Batch 1 | 55 | 0.3 | 0.59 | 49 |
| Batch 2 | 90 | 0.26 | 0.54 | 52 |
| Batch 3 | 110 | 0.27 | 0.53 | 49 |

|  | Cohesion 2000 μm | Wettability (mm) | Dispersibility (% product wetted after 2 minutes - constant value subsequently) |
|---|---|---|---|
| Single-effect spray drying control | 71 | 0 Remains at the surface of the water | 0 |
| "Non-optimized" air broom control | 65 | 0 Penetration into the water; no decanting | 0 |
| Batch 1 | 59 | 2 | 70 |
| Batch 2 | 59 | 0 Penetration into the water; no decanting | 80 |
| Batch 3 | 57 | 0 Penetration into the water; no decanting | 80 |

Entirely logically, it is observed that the conventional microalgal flour ("single-effect spray drying" control), characterized by "cohesive" particles, does not become sufficiently hydrated to decant, whereas the microalgal flour in accordance with the invention does this readily, despite its cohesive character. Thus, the conventional microalgal flour is deposited on the surface of the water without penetrating into the water. Conversely, the microalgal flour in accordance with the invention hydrates well and does not decant at the bottom of the beaker.

With regard to the standard "air broom" test, it is observed that the powder obtained does not have any wettability or water-dispersibility.

The invention claimed is:

1. A process for preparing a microalgal flour, the size of the flour particles being between 30 and 150 μm in diameter said flour having a compressibility, as measured on HOSOKAWA powder tester, of between 45% and 55%, the microalgal flour having:
  a flow value, determined according to a test A, of between 55% and 60% by weight for the oversize at 2000 μm;
  a dispersibility and wettability, expressed, according to a test B, by the height of the product decanted in a beaker, having a value of between 0 and 2 mm; and
  a degree of wetting having a value of more than 70% of the total powder;
wherein the process comprises:
  1) preparing an emulsion of lipid-rich microalgal flour in water with a solids content of between 15% and 50% by dry weight, wherein this emulsion is prepared by mechanically lysing microalgal cells and wherein the lipid-rich microalgal flour comprises at least 10% by dry weight of lipids,
  2) introducing this emulsion into a high-pressure homogenizer,
  3) spraying this emulsion in a flat-bottom spray dryer equipped with an air broom for sweeping the spray drying chamber with low-pressure air in its lower portion, while making adjustments to ensure that:
    a) the temperature of the main drying air is between 160° and 240°C.,
    b) the temperature of the air in the air broom portion is at most 70°C.,
    c) the ratio of the flow rate of the air from the air broom to the flow rate of the main drying air has a value greater than ⅓ d) the temperature of the cooling air is between 25° and 35°C., such that the flour leaving the spray dryer has a temperature of between 60°C. and 90°C., 4) collecting the microalgal flour thus obtained.

2. The method as claimed in claim 1, wherein the temperature of the air in the air broom portion is at most 65°C.

3. The method as claimed in claim 1, wherein the ratio of the flow rate of the air from the air broom to the flow rate of the main drying air has a value between ⅓ and ½.

* * * * *